United States Patent
Jin et al.

(10) Patent No.: US 11,136,298 B2
(45) Date of Patent: *Oct. 5, 2021

(54) METHOD FOR PRODUCING FULLERENE DERIVATIVE

(71) Applicants: SHOWA DENKO K.K., Tokyo (JP); MITSUBISHI CORPORATION, Tokyo (JP)

(72) Inventors: Tienan Jin, Sendai (JP); Weili Si, Boulder, CO (US); Yoshinori Yamamoto, Sendai (JP); Takeshi Igarashi, Chiba (JP)

(73) Assignees: SHOWA DENKO K.K., Tokyo (JP); MITSUBISHI CORPORATION, Tokyo (JP)

( * ) Notice: Subject to any disclaimer, the term of this patent is extended or adjusted under 35 U.S.C. 154(b) by 0 days.

This patent is subject to a terminal disclaimer.

(21) Appl. No.: 16/680,570

(22) Filed: Nov. 12, 2019

(65) Prior Publication Data

US 2020/0095209 A1 Mar. 26, 2020

Related U.S. Application Data

(62) Division of application No. 15/509,080, filed as application No. PCT/JP2015/075186 on Sep. 4, 2015, now Pat. No. 10,526,293.

(30) Foreign Application Priority Data

Sep. 8, 2014 (JP) .................................. 2014-182133
Oct. 22, 2014 (JP) .................................. 2014-215192

(51) Int. Cl.
| | | |
|---|---|---|
| C07C 22/04 | (2006.01) | |
| C07D 241/38 | (2006.01) | |
| C01B 32/154 | (2017.01) | |
| C07C 67/343 | (2006.01) | |
| C07C 69/76 | (2006.01) | |
| C07C 41/30 | (2006.01) | |
| C07C 43/21 | (2006.01) | |
| C07D 333/78 | (2006.01) | |
| C07C 1/26 | (2006.01) | |
| C07C 2/86 | (2006.01) | |
| C07D 241/36 | (2006.01) | |
| C07C 13/64 | (2006.01) | |
| C07C 17/266 | (2006.01) | |
| C07C 17/32 | (2006.01) | |
| C07C 25/22 | (2006.01) | |
| C07D 241/42 | (2006.01) | |
| A61K 31/5377 | (2006.01) | |

(Continued)

(52) U.S. Cl.
CPC ........ *C07D 241/38* (2013.01); *A61K 31/5377* (2013.01); *A61K 31/55* (2013.01); *C01B 32/154* (2017.08); *C07C 1/26* (2013.01); *C07C 2/86* (2013.01); *C07C 13/64* (2013.01); *C07C 17/266* (2013.01); *C07C 17/32* (2013.01); *C07C 25/22* (2013.01); *C07C 41/30* (2013.01); *C07C 43/21* (2013.01); *C07C 67/343* (2013.01); *C07C 69/76* (2013.01); *C07D 241/36* (2013.01); *C07D 241/42* (2013.01); *C07D 333/78* (2013.01); *C07B 61/00* (2013.01); *C07C 2523/06* (2013.01); *C07C 2523/34* (2013.01); *C07C 2523/745* (2013.01); *C07C 2604/00* (2017.05)

(58) Field of Classification Search
None
See application file for complete search history.

(56) References Cited

U.S. PATENT DOCUMENTS

| | | |
|---|---|---|
| 4,265,891 A | 5/1981 | Collington et al. |
| 4,649,212 A | 3/1987 | Durr |

(Continued)

FOREIGN PATENT DOCUMENTS

| | | |
|---|---|---|
| EP | 2457898 A1 | 5/2012 |
| JP | 55-36475 A | 3/1980 |

(Continued)

OTHER PUBLICATIONS

Database Registry Chemical Abstracts Service, Columbus, Ohio, Accession No. RN 135100-98-0, Entered STN: Jul. 26, 1991.*

(Continued)

*Primary Examiner* — Samantha L Shterengarts
(74) *Attorney, Agent, or Firm* — Sughrue Mion, PLLC

(57) ABSTRACT

This method for producing a fullerene derivative is a method for producing a fullerene derivative having a partial structure shown by formula (1) by reacting a predetermined halogenated compound and two carbon atoms adjacent to each other for forming a fullerene skeleton in a mixed solvent of an aromatic solvent and an aprotic polar solvent having a C=O or S=O bond in the presence of at least one metal selected from the group comprising manganese, iron, and zinc;

[Chem. 1]

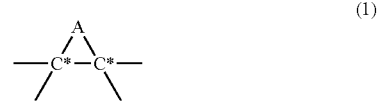

(1)

(in formula (1), C* are each carbon atoms adjacent to each other for forming a fullerene skeleton, A is a linking group having 1-4 carbon atoms for forming a ring structure with two C*, in which a portion thereof may be a substituted or condensed group).

1 Claim, No Drawings

(51) Int. Cl.
*A61K 31/55* (2006.01)
*C07B 61/00* (2006.01)

(56) References Cited

U.S. PATENT DOCUMENTS

| 2007/0155729 | A1 | 7/2007 | Morgan et al. |
| 2017/0253567 | A1 | 9/2017 | Jin et al. |

FOREIGN PATENT DOCUMENTS

| JP | 58-41861 | A | 3/1983 |
| JP | 58-49345 | A | 3/1983 |
| JP | 58-65249 | A | 4/1983 |
| JP | 63-48229 | A | 2/1988 |
| JP | 2-172986 | A | 7/1990 |
| JP | 3-14525 | A | 1/1991 |
| JP | 8-503980 | A | 4/1996 |
| JP | 2000-034314 | A | 2/2000 |
| JP | 2003-113128 | A | 4/2003 |
| JP | 2004-315444 | A | 11/2004 |
| JP | 2008-184410 | A | 8/2008 |
| JP | 2012-107025 | A | 6/2012 |
| WO | 02/15691 | A1 | 2/2002 |

OTHER PUBLICATIONS

Beatriz M. Illescas, et al., "Reaction of $C_{60}$ with Sultines: Synthesis, Electrochemistry, and Theoretical Calculations of Organofullerene Acceptors", J. Org. Chem., 1997, pp. 7585-7591, vol. 62.

Guan-Vvu Wang, et al., "[60]Fullerene-Fused Lactones: Manganese(III) Acetate-Mediated Synthesis and Novel Reductive Ring Opening", Organic Letters, 2006, pp. 1355-1358, vol. 8, No. 7.

Hudhomme et al: "Diels-Alder cycloaddition as an efficient tool for linking p-donors onto fullerene $C_{60}$", Comptes Rendus-Chimie, Elsevier, Paris, FR, vol. 9, No. 7-8, Jul. 1, 2006 (Jul. 1, 2006), pp. 881-891.

Shirong Lu, et al., "Co-Catalyzed Radical Cycloaddition of [60]Fullerene with Active Dibromides: Selective Synthesis of Carbocycle-Fused Fullerene Monoadducts", Organic Letters, 2013, pp. 4030-4033, vol. 15, No. 15.

Guan-Wu Wang, et al., "Synthesis of [60]Fullerene Acetals and Ketals: Reaction of [60]Fullerene with Aldehydes/Ketones and Alkoxides", Journal of Organic Chemistry, 2007, pp. 4779-4783, vol. 72, No. 13.

M. Prato, et al., "[3+2] and [4+2] Cycloadditions of $C_{60}$", J. Am. Chem. Soc., 1993, pp. 1594-1595, vol. 115.

International Search Report of PCT/JP2015/075186, dated Nov. 2, 2015. [PCT/ISA/237].

Jin et al.; DMSO: An Efficient Catalyst for the Cyclopropanation of C60, C70, SWNTs, and Graphene through the Bingel Reaction; Ind. Eng. Chem. Res., 2015, 54 (11), 2879-2885; 7 pages.

Jan C. Hummelen, et al., "Preparation and Characterization of Fulleroid and Methanofullerene Derivatives", J. Org. Chem., 1995, pp. 532-538, vol. 60.

Zhongwen Wang, et al., "Monoalkylation of $C_{60}$ and $C_{70}$ with Zn and Active Alkyl Bromides", Journal of Organic Chemistry, 2003, pp. 3043-3048, vol. 68, No. 8.

Communication dated Jan. 2, 2018, from the European Patent Office in counterpart European Application No. 15840111.7.

Communication dated Jun. 16, 2020, from the Japanese Patent Office in application No. 2019-135476.

Andrey Sheshenev et al. "Stereo- and regiocontrol in ene-dimerisation and trimerisation of 1-trimethylsilyl-3-phenylcyclopropene", Tetrahedron, vol. 65, No. 51, 2009, pp. 10552-10564.

W Kirmse et al.,"Zerfall von 1-Arylcyclopropandiazonium-Ionen", Chemische Berichte, vol. 119, No. 12, 1986, pp. 3694-3703 (11 pages total).

\* cited by examiner

METHOD FOR PRODUCING FULLERENE DERIVATIVE

CROSS REFERENCE TO RELATED APPLICATIONS

This application is a divisional of application Ser. No. 15/509,080 filed Mar. 6, 2017, which is a National Stage of International Application No. PCT/JP2015/075186 filed Sep. 4, 2015, claiming priority based on Japanese Patent Application Nos. 2014-182133, filed Sep. 8, 2014, and 2014-215192, filed Oct. 22, 2014, the contents of all of which are incorporated herein by reference in their entirety.

TECHNICAL FIELD

The present invention relates to a method for producing a fullerene derivative.

BACKGROUND ART

Fullerene derivatives have received attention in the fields of physics and chemistry due to the unique characteristics thereof. Particularly, since a mass synthesis method by arc discharge was established in 1990, research thereabout has gained more attention. Fullerene derivatives are known as materials useful as electronic materials, semiconductors, physiologically active substances, and so on.

Many fullerene derivatives have been reported. Among them, research is actively underway on derivatives having a structure in which a cyclic structure including hydrocarbon is condensed to a fullerene skeleton as acceptor materials used for organic thin film solar cells and biochemical probes utilizing the photoresponsiveness due to the high heat resistance thereof.

CITATION LIST

Non-Patent Literature

[Non-Patent Document 1]
Jan C. Hummelen et al. J. Org. Chem. 1995, 60, 532-538.
[Non-Patent Document 2]
M. Prato et al. J. Am. Chem. Soc. 1993, 115, 1594-1595.
[Non-Patent Document 3]
Bratriz M. Illescas et al. J. Org. Chem. 1997, 62, 7585-7591.
[Non-Patent Document 4]
Shirong Lu et al. Organic Letters. 2013, Vol. 15, No. 15, 4030-4033.

SUMMARY OF INVENTION

Technical Problem

However, there was a problem that a method for producing a fullerene derivative in which a cyclic hydrocarbon group is condensed to a fullerene skeleton differs depending on the number of carbon atoms forming a ring. From the viewpoint of efficient production, the preparation method has many problems in that the method is a complicated method requiring a multi-step reaction or a method for which a special substrate is necessarily used.

For example, a method of preparing PCBM, which is a fullerene derivative in which a cyclopropane structure is condensed to a fullerene skeleton and is a representative material for an acceptor material for organic thin film solar cells, is described in Non-patent literature 1. Specifically, in order to prepare PCBM, $C_{60}$ is reacted with a diazo compound to obtain a fulleroid first, and then a fulleroid is isomerized under reflux conditions in orthodichlorobenzene with a boiling point of 180° C. to prepare PCBM. In this manner, a reaction of two steps is necessary for preparing PCBM, and there are manufacturing problems such as using a dangerous diazo compound or requiring a high temperature.

A method for producing a fullerene derivative used for biochemical applications, in which a cyclopropane structure is condensed to a fullerene skeleton, is described in Non-Patent Document 2. That is, a fullerene derivative, in which a cyclopropane structure is condensed to a fullerene skeleton, is prepared by reacting a trimethylenemethane compound generated in the system by thermal decomposition of a methylenecyclopropane compound with $C_{60}$. However, a methylenecyclopropane compound to be a raw material is limited, and the preparation of the methylenecyclopropane compound itself is also complicated.

A method for producing a fullerene derivative in which a cyclohexane structure is condensed to a fullerene skeleton by reacting orthoquinodimethane with $C_{60}$ is described in Non-Patent Document 3. However, this method is impossible to be applied to the preparation of structures other than a 6-membered ring structure due to using a (4+2) cyclic addition reaction.

Recent research has succeeded in producing a fullerene derivative, in which a cyclopropane, cyclopentane or cyclohexane structure is condensed to a fullerene skeleton by reacting a dihalogenated compound with $C_{60}$ using a Co complex as a catalyst in the presence of Mn and under mild conditions of room temperature, in a high yield (Non-Patent Document 4). However, also in this method, it is necessary to use an expensive metal catalyst, and thus there is a practical problem.

The present invention has been made in consideration of the circumstances described above, and an object of the invention is to provide a method for effectively producing a fullerene derivative in which a cyclic carbon chain is condensed to a fullerene skeleton under mild conditions irrespective of the number of carbon atoms forming a ring.

Solution to Problem

The inventors of the present invention found that a fullerene derivative in which a cyclic carbon chain is condensed to a fullerene skeleton can be effectively prepared under mild conditions irrespective of the number of carbon atoms forming a ring, by reacting two carbon atoms adjacent to each other for forming a fullerene skeleton with a specific halogenated compound in a mixed solvent of an aromatic solvent and an aprotic polar solvent having a C=O or S=O bond in the presence of at least one metal selected from the group consisting of manganese, iron and zinc.

In other words, the present invention includes the following configurations.

(1) A method for producing a fullerene derivative of the present invention is a method for producing a fullerene derivative having a partial structure represented by Formula (1), by reacting two carbon atoms adjacent to each other for forming a fullerene skeleton with a halogenated compound represented by Formula (2) in a mixed solvent of an aromatic solvent and an aprotic polar solvent having a C=O or S=O bond in the presence of at least one metal selected from the group consisting of manganese, iron and zinc. In Formula (1), C* each represent carbon atoms adjacent to each other for forming a fullerene skeleton, and A represents a linking group with 1 to 4 carbon atoms for forming a ring structure or a functional group in which the linking group is partially substituted or condensed. In Formula (2), A represents a linking group with 1 to 4 carbon atoms or a functional group in which the linking group is partially substituted or condensed, and each X independently represents a halogen atom.

[Chem. 1]

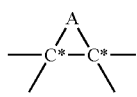
(1)

[Chem. 2]

(2)

(2) In the method for producing a fullerene derivative according to the above-described (1), the linking group with 1 to 4 carbon atoms for A may be partially substituted by an aromatic group, a heteroaromatic group, an alkoxycarbonyl group or an alkylidene group.

(3) In the method for producing a fullerene derivative according to the above-described (1), the linking group with 1 to 4 carbon atoms for A may partially form a condensed-ring structure or a polycyclic structure including an aromatic ring or a heteroaromatic ring with an aromatic ring or a heteroaromatic ring.

(4) In the method for producing a fullerene derivative according to any one of the above-described (1) to (3), the aprotic polar solvent may be one or more of the group consisting of dimethyl sulfoxide (DMSO) and dimethylformamide (DMF).

(5) In the method for producing a fullerene derivative according to any one of the above-described (1) to (4), the aromatic solvent may be o-dichlorobenzene.

(6) In the method for producing a fullerene derivative according to any one of the above-described (1) to (5), the halogen atom (X) may be Br.

(7) In the method for producing a fullerene derivative according to any one of the above-described (1) to (6), the metal may be Mn, and the aprotic polar solvent may be DMF.

(8) In the method for producing a fullerene derivative according to any one of the above-described (1) to (6), the metal may be Fe, and the aprotic polar solvent may be DMSO.

(9) In the method for producing a fullerene derivative according to any one of the above-described (1) to (6), the metal may be Mn or Zn, and the aprotic polar solvent may be DMSO.

Advantageous Effects of Invention

According to the method for producing a fullerene derivative of the present invention, a fullerene derivative useful as a functional material, in which a cyclic carbon chain is condensed to a fullerene skeleton, can be easily prepared under mild conditions. Further, since similar reaction conditions can be applied irrespective of the number of carbon atoms forming a ring (i.e., the number of carbon atoms of a raw material), reaction conditions and operations can be standardized when a plurality of fullerene derivatives are prepared, and as a result, a target fullerene derivative can be effectively prepared.

DESCRIPTION OF EMBODIMENTS

Hereinafter, the configuration of the embodiment of the present invention will be described. The present invention can be implemented with appropriate modifications within a range that does not change the gist thereof.

(Method for producing fullerene derivative) A method for producing a fullerene derivative according to an aspect of the present invention is a method for producing a fullerene derivative having a partial structure represented by Formula (1), by reacting two carbon atoms adjacent to each other for forming a fullerene skeleton with a halogenated compound represented by Formula (2) in a mixed solvent of an aromatic solvent and an aprotic polar solvent having a C=O or S=O bond in the presence of at least one metal selected from the group consisting of manganese, iron and zinc.

In Formula (1), C* each represent carbon atoms adjacent to each other for forming a fullerene skeleton, and A represents a linking group with 1 to 4 carbon atoms for forming a ring structure or a functional group in which the linking group is partially substituted or condensed. Here, when there are two or more linking routes connecting two C*, the route having the smallest number of carbon atoms is a linking group. In Formula (2), A represents a linking group with 1 to 4 carbon atoms or a functional group in which the linking group is partially substituted or condensed, and each X independently represents a halogen atom.

The "fullerene derivative" refers to a compound having a structure formed by addition of a specific functional group with respect to the fullerene skeleton, and the "fullerene skeleton" refers to a carbon skeleton constituting a closed shell structure derived from a fullerene.

[Chem. 3]

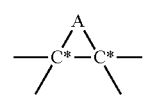
(1)

[Chem. 4]

(2)

Here, a "linking group with 1 to 4 carbon atoms or a functional group in which the linking group is partially substituted or condensed" will be described by way of a specific example. For example 1,2-bis(bromomethyl)benzene is represented by the following Formula (3).

[Chem. 5]

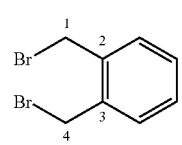
(3)

As shown in Formula (3), 1,2-bis(bromomethyl)benzene has four carbon atoms connecting two Br, and thus has a linking group with four carbon atoms. Further, the second carbon atom and the third carbon atom in Formula (3) are condensed with a benzene ring. That is, in 1,2-bis(bromomethyl)benzene, A of Formula (2) is represented as a functional group in which the linking group with four carbon atoms is partially condensed.

Furthermore, as another example, dibromomethylbenzene is represented by the following Formula (4).

[Chem. 6]

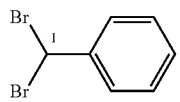

(4)

As in Formula (3), dibromomethylbenzene represented by Formula (4) has one carbon atom connecting two Br, and thus has a linking group with one carbon atom. Hydrogen connected to the first carbon in Formula (4) is substituted by an aromatic group. That is, in dibromomethylbenzene, A of Formula (2) is represented as a functional group in which the linking group with one carbon atom is partially substituted.

Further, for example, 2,3-bis(bromomethyl)quinoxaline is represented by the following Formula (5).

[Chem. 7]

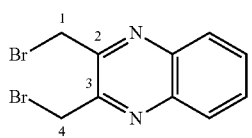

(5)

As in Formula (3), 2,3-bis(bromomethyl)quinoxaline represented by Formula (5) has four carbon atoms connecting two Br, and thus has a linking group with four carbon atoms. Moreover, the second carbon and the third carbon in Formula (5) are condensed with a heteroaromatic ring. The heteroaromatic ring forms a polycyclic structure as a whole by further being condensed with an aromatic ring.

That is, in 2,3-bis(bromomethyl)quinoxaline, A of Formula (2) is represented as a functional group in which the linking group with four carbon atoms is partially condensed with a polycyclic structure including an aromatic ring or a heteroaromatic ring.

Further, for example, 1,3-dibromoindane is represented by the following Formula (6).

[Chem. 8]

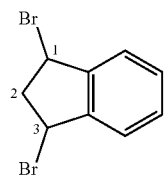

(6)

As in Formula (3), 1,3-dibromoindane represented by Formula (6) has a linking route with three carbon atoms and a linking route with four carbon atoms connecting two Br. As described above, in an aspect of the present invention, when there are two or more linking routes connecting two C*, the route having the smallest number of carbon atoms is a linking group. Therefore, 1,3-dibromoindane has a linking group with three carbon atoms. Further, the first carbon and the third carbon in Formula (6) are condensed with an aromatic ring. A five-membered ring is formed by an aromatic ring and a linking group by bonding the aromatic ring to two carbon atoms of the linking group, and thereby a polycyclic structure is formed as a whole.

That is, in 1,3-dibromoindane, A of Formula (2) is represented as a functional group in which the linking group with three carbon atoms forms a condensed-ring structure with an aromatic ring.

Hereinafter, details of each element will be explained with a description of a fullerene derivative.

First, a compound having a fullerene skeleton and a halogenated compound are prepared.

The compound having a fullerene skeleton may be obtained by a known method (e.g., a method using arc discharge) or the like.

For the compound having a fullerene skeleton, $C_{60}$, $C_{70}$, $C_{76}$, $C_{78}$, $C_{82}$, $C_{84}$, $C_{90}$, $C_{94}$, $C_{96}$, $C_{120}$, $C_{200}$ or the like may be used. Among them, the number of carbon atoms of the fullerene skeleton is preferably 60 to 120, and $C_{60}$ is more preferable. A compound with high purity may be easily obtained using a fullerene skeleton with few carbon atoms, and particularly, $C_{60}$ enables a compound with high purity to be easily obtained as compared with other fullerene skeletons.

The halogenated compound is not particularly limited as long as it is represented by Formula (2), and may be obtained using a known method. Examples of the halogenated compound include a halogenated compound having a heterocycle such as 1,2-bis(bromomethyl)benzene, dibromomethylbenzene, 1-dibromomethyl-3-fluorobenzene, 3,4-bis(bromomethyl)-2,5-dimethylthiophene, 2,3-bis(bromomethyl)quinoxaline or the like, a halogenated compound having a 5-membered ring such as 1,3-dibromo-2,3-dihydro-$^1$H-indene or the like, a halogenated compound having a halogen element such as F or Br in addition to a reacting halogen element such as 1-bromo-4-(1,3-dibromo-3-(4-fluorophenyl)propylbenzene or the like, a halogenated compound to which an allyl compound is added, and so on.

Although a case in which a halogen element (X in Formula (2)) in a halogenated compound is bromine (Br) was described above, it may be a substance in which the bromine element is replaced with a halogen element such as iodine (I), chlorine (Cl), fluorine (F) or the like. However, a halogen element is preferably bromine (Br). This is because a brominated compound allows the reaction to proceed relatively easily as compared with a case of a chlorinated compound or a fluorinated compound, and is generally less expensive and more easily obtained than an iodinated compound.

Next, a compound having a fullerene skeleton and a halogenated compound are added to a mixed solution of an aromatic solvent and an aprotic polar solvent having a C=O or S=O bond.

The aromatic solvent represents a solvent formed of a compound having an aromatic ring. The aromatic solvent is not particularly limited, and examples thereof include benzene, toluene, xylene, o-dichlorobenzene (ODCB), trichlorobenzene, and so on.

The aromatic solvent is preferably a halogen-substituted solvent, and is more preferably o-dichlorobenzene. The solubility of both of the compound having a fullerene skeleton and the halogenated compound to be a raw material is increased in a halogen-substituted solvent. O-dichlorobenzene imparts a high solubility to both of the compound having a fullerene skeleton and the halogenated compound to be a raw material, and is capable of increasing a reaction concentration. Therefore, it is preferable to use o-dichlorobenzene in that productivity is increased through the improvement of the reaction rate and a reaction vessel can be reduced in size.

The aprotic polar solvent having a C=O or S=O bond refers to a polar solvent which has no proton-donor ability and partially includes a C=O or S=O bond.

For example, dimethylsulfoxide (DMSO), dimethylformamide (DMF) or the like may be used. Dimethylsulfoxide or dimethylformamide is preferable due to allowing the reaction to proceed easily.

In the presence of the mixed solution and at least one metal selected from the group consisting of manganese, iron and zinc, two carbon atoms adjacent to each other for forming a fullerene skeleton of the compound having a fullerene skeleton are reacted with a halogenated compound represented by Formula (2).

Light, heat or the like is not particularly required for the reaction, and the reaction automatically proceeds by adding a compound having a fullerene skeleton and a halogenated compound to the mixed solution in the presence of a predetermined metal.

When the reaction proceeds under the reaction conditions, a fullerene derivative useful as a functional material in which a cyclic carbon chain is condensed to a fullerene skeleton can be easily prepared in a high yield under mild conditions. Further, similar conditions can be applied irrespective of the number of carbon atoms forming a ring (i.e., the number of carbon atoms of a raw material). Therefore, when a plurality of fullerene derivatives are prepared, the reaction conditions and operations can be standardized.

When a compound having a fullerene skeleton to be a raw material is a fullerene with no substituent, the fullerene derivative obtained therefrom is a monocyclic adduct in which only one cyclic carbon chain formed of a partial structure represented by Formula (1) is added to a fullerene skeleton, a dicyclic adduct in which two cyclic carbon chains formed of a partial structure represented by Formula (1) are added to a fullerene skeleton, a polycyclic adduct in which three or more cyclic carbon chains formed of a partial structure represented by Formula (1) are added to a fullerene skeleton or a mixture thereof. In the method of the present invention, the number of cyclic carbon chains added to the fullerene derivative to be obtained may be selectively set depending on a metal content and/or an amount of a halogenated compound used during the reaction, and each of the fullerene derivatives whose main component is a monocyclic adduct, a dicyclic adduct, or a polycyclic adduct may be prepared as necessary.

Furthermore, the "main component" used herein refers to a component which is included at 50 mol % or more in a mixture of fullerene derivatives having a different number of partial structures represented by Formula (1). Further, in a method for producing a fullerene derivative according to an aspect of the present invention, reproducibility for each processing batch that was difficult to be realized in the conventional method for producing a fullerene derivative can be obtained.

As a method for producing a fullerene derivative according to an aspect of the present invention, it is preferable that a metal to be added is Mn, and an aprotic polar solvent is DMF. In this case, a fullerene derivative having three or more partial structures represented by Formula (1) in one fullerene skeleton can be obtained in a higher yield. That is, a fullerene derivative in which a fullerene derivative having three or more partial structures represented by Formula (1) in one fullerene skeleton is the entire main component can be selectively obtained.

In addition to this, as a method for producing a fullerene derivative according to an aspect of the present invention, it is preferable that a metal to be added is Fe, and an aprotic polar solvent is DMSO. In this case, a fullerene derivative having one partial structure represented by Formula (1) in one fullerene skeleton can be obtained in a higher yield. That is, a fullerene derivative in which a fullerene derivative having one partial structure represented by Formula (1) in one fullerene skeleton is the entire main component can be selectively obtained.

Furthermore, as a method for producing a fullerene derivative according to an aspect of the present invention, it is preferable that a metal to be added is Mn or Zn, and an aprotic polar solvent is DMSO. In this case, a fullerene derivative having two partial structures represented by Formula (1) in one fullerene skeleton can be obtained in a higher yield. That is, a fullerene derivative in which a fullerene derivative having two partial structures represented by Formula (1) in one fullerene skeleton is the entire main component can be selectively obtained.

A temperature during the reaction is preferably in the range of 0° C. to 60° C. A fullerene derivative can be produced more effectively within this temperature range. Further, in the temperature range, room temperature is preferable. When the temperature is room temperature, heating and cooling is not necessary, and this is also excellent in that no special equipment is required, and a fullerene derivative can be prepared easily and inexpensively.

Further, the reaction time is preferably in the range of 1 to 100 hours, and is more preferably in the range of 10 to 50 hours. When the reaction time is within this range, the reaction can proceed sufficiently, and it is realistic from the viewpoint of productivity.

The reaction atmosphere is preferably an inert gas atmosphere. When the reaction is performed in an inert gas, the generation of unnecessary side reactions or the like can be suppressed.

EXAMPLES

Hereinafter, the present invention will be described in detail on the basis of examples. Moreover, the invention is not limited to the examples.

Example 1-1

For Example 1-1, $C_{60}$ (21.6 mg, 0.03 mmol) was used as a compound having a fullerene skeleton and dibromobenzene 1a (31.6 mg, 0.12 mmol, 4 mol equivalents) was used as a halogenated compound. Further, ODCB (4 mL) as an aromatic solvent and DMSO (0.4 mL) as an aprotic polar solvent were used for the mixed solution. Moreover, Mn powder (15 mg, 0.27 mmol, 9 mol equivalents) was used as a metal used in the reaction, and the reaction was performed for 12 hours at room temperature under an Ar atmosphere.

[Chem. 9]

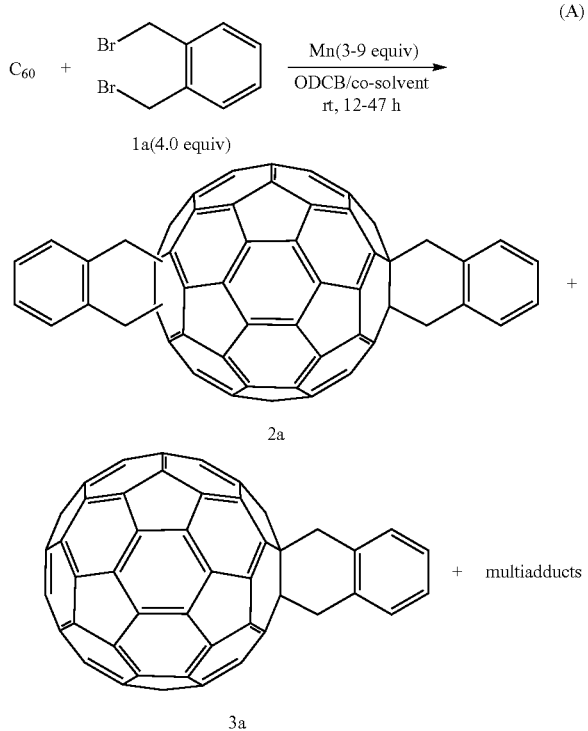

The reaction may be represented by Formula (A). As represented by Formula (A), a dicyclic adduct 2a in which two cyclic substances are added to a fullerene skeleton, a monocyclic adduct 3a in which one cyclic substance is added to a fullerene skeleton, a polycyclic adduct with three or more cyclic substances, or a mixture thereof is formed by the reaction.

The product after the reaction was analyzed by high performance liquid chromatography (HPLC). HPLC was performed under the following conditions.

Column: Cosmosil Buckyprep manufactured by Nacalai Tesque, Inc. (4.6 mm I.D.×250 mm)
Mobile phase: toluene
Flow rate: 0.6 mL/min
Detection: UV 320 nm
Measurement temperature: 16° C.

Here, $C_{70}$ was used as an internal standard. At the same time, an abundance ratio of non-reacted $C_{60}$ was measured to determine the progress status of the reaction.

Further, each of separated materials was identified by a $^1$H-NMR spectrum and $^{13}$C-NMR spectrum. A JEOL JMTC-270/54/SS (400 MHz) manufactured by JASTEC Corporation was used in the measurement. Moreover, identification by a high resolution mass spectrum (HRMS) was also conducted. An APEX III manufactured by BRUKER was used for the result.

The data of the dicyclic adduct 2a is shown below.

2a: brown solid; $^1$H NMR (400 MHz, $CDCl_3/CS_2$=1/4) δ 3.49-5.00 (8H, m), 7.37-7.83 (8H, m); $^{13}$C NMR (100 MHz, $CDCl_3/CS_2$=1/4) δ 43.52, 44.11, 44.46, 44.79, 45.22, 63.93, 64.05, 64.34, 64.42, 64.65, 127.26, 127.51, 127.69, 137.05, 137.18, 137.45, 140.88, 141.15, 142.38, 142.58, 143.31, 143.99, 144.13, 144.31, 144.44, 144.75, 144.93, 144.99, 145.52, 145.91, 146.26, 146.38, 146.73, 147.28, 147.66, 148.17, 148.79, 149.14, 154.32, 154.74, 159.80, 160.94. HRMS (MALDI) $C_{76}H_{16}$ $[M]^+$: 928.1247, found 928.1247.

Example 1-2 and Comparative Examples 1-1 to 1-5

The study was performed in the same manner as in Example 1-1 except that the presence or absence of an aprotic polar solvent or Mn was changed. However, the reaction time was 44 hours only in Comparative Example 1-2. Further, ethanol which is a protic polar solvent was used instead of an aprotic polar solvent in Comparative Example 1-5. The results of the study are shown in Table 1. In Table 1, $CH_3CN$ is acetonitrile, THF is tetrahydrofuran and EtOH is ethanol.

Examples 1-3

For Examples 1 to 3, $C_{60}$ (21.6 mg, 0.03 mmol) was used as a compound having a fullerene skeleton and 1,2-bis (bromomethyl)benzene (17.4 mg, 0.066 mmol, 2.2 mol equivalents) was used as a halogenated compound. Further, ODCB (4 mL) as an aromatic solvent and DMSO (0.3 mL) as an aprotic polar solvent were used for the mixed solution. Moreover, Mn powder (5 mg, 0.09 mmol, 3 mol equivalents) was used as a metal used in the reaction, and the reaction was performed for 47 hours at room temperature under an Ar atmosphere. The results are shown in Table 1.

Examples 1-4 and 1-5, Comparative Examples 1-6 to 12

The study was performed in the same manner as in Example 1-3 except that a metal used in the reaction was changed. However, the reaction time was 20 hours only in Comparative Example 1-4. The results of the study are shown in Table 1.

TABLE 1

| | Metal (mol equivalents) | Polar solvent | Abundance ratio | | | | Yield of fullerene derivative (%) |
| | | | Dicyclic adduct (%) | Monocyclic adduct (%) | Polycyclic adduct (%) | Collected $C_{60}$ (%) | |
| --- | --- | --- | --- | --- | --- | --- | --- |
| Example 1-1 | Mn (9) | DMSO | 56 | — | 21 | — | 78 |
| Example 1-2 | Mn (9) | DMF | 0 | 0 | 96 | 0 | 96 |
| Comparative Example 1-1 | — | DMSO | 0 | 0 | 0 | 95 | 0 |
| Comparative Example 1-2 | Mn (9) | — | 0 | 0 | 0 | 95 | 0 |
| Comparative Example 1-3 | Mn (9) | $CH_3CN$ | 0 | 0 | 0 | 95 | 0 |
| Comparative Example 1-4 | Mn (9) | THF | 0 | 0 | 0 | 95 | 0 |

TABLE 1-continued

|  | Metal (mol equivalents) | Polar solvent | Dicyclic adduct (%) | Monocyclic adduct (%) | Polycyclic adduct (%) | Collected $C_{60}$ (%) | Yield of fullerene derivative (%) |
|---|---|---|---|---|---|---|---|
| Comparative Example 1-5 | Mn (9) | EtOH | 0 | 0 | 0 | 95 | 0 |
| Example 1-3 | Mn (3) | DMSO | 87 | 0 | 12 | 0 | 99 |
| Example 1-4 | Zn (3) | DMSO | 58 | 15 | 10 | 0 | 73 |
| Example 1-5 | Fe (3) | DMSO | 0 | 54 | 0 | 44 | 54 |
| Comparative Example 1-6 | $MnO_2$ (3) | DMSO | 0 | 0 | 0 | 99 | 0 |
| Comparative Example 1-7 | $Mn(OAc)_3 \cdot 2H_2O$ (3) | DMSO | 0 | 0 | 0 | 99 | 0 |
| Comparative Example 1-8 | $MnCl_2 \cdot H_2O$ (3) | DMSO | 0 | 0 | 0 | 99 | 0 |
| Comparative Example 1-9 | Mg (3) | DMSO | 0 | 0 | 0 | 99 | 0 |
| Comparative Example 1-10 | Cu (3) | DMSO | 0 | 0 | 0 | 99 | 0 |
| Comparative Example 1-11 | Pd/C (3) | DMSO | 0 | 0 | 0 | 99 | 0 |
| Comparative Example 1-12 | Raney Ni (3) | DMSO | 0 | 0 | 0 | 99 | 0 |

Abundance ratio (spans Dicyclic/Monocyclic/Polycyclic adduct columns)

As shown in Examples 1-1 to 1-5, a fullerene derivative in which a cyclic substance is added to a fullerene skeleton can be selectively prepared using the method of the present invention. Further, when Example 1-1 is compared with Example 1-3, it can be seen that the reaction of adding a plurality of cyclic substances to a fullerene skeleton is suppressed and the yield of the dicyclic adduct is increased by decreasing the number of mol equivalents of the metal.

In contrast, as shown in Comparative Examples 1-1 and 1-2, it can be seen that adducts are not produced in the absence of a metal and an aprotic polar solvent. Further, as shown in Comparative Examples 1-3 to 1-5, the reaction does not proceed when an aprotic polar solvent with no C=O or S=O bond or a protic polar solvent is used. Moreover, there is no effect with an oxide even if it contains Mn as shown in Comparative Examples 1-6 to 1-8, and there is no effect unless an appropriate metal is selected as shown in Comparative Examples 1-9 to 1-12.

Examples 2-1 to 2-10

Next, a fullerene derivative in which a cyclic substance is added to a fullerene skeleton was prepared by varying the halogenated compound to be added.

$C_{60}$ (21.6 mg, 0.03 mmol) was used as a compound having a fullerene skeleton and reacted with a halogenated compound (2.2 mol equivalents). At this time, ODCB (4 mL) as an aromatic solvent and DMSO (0.3 mL) as an aprotic polar solvent were used for the mixed solution. Moreover, Mn powder (5 mg, 0.09 mmol, 3 mol equivalents) was used as a metal used in the reaction, and the reaction of Reaction Formula (B) was performed at room temperature under an Ar atmosphere.

[Chem. 10]

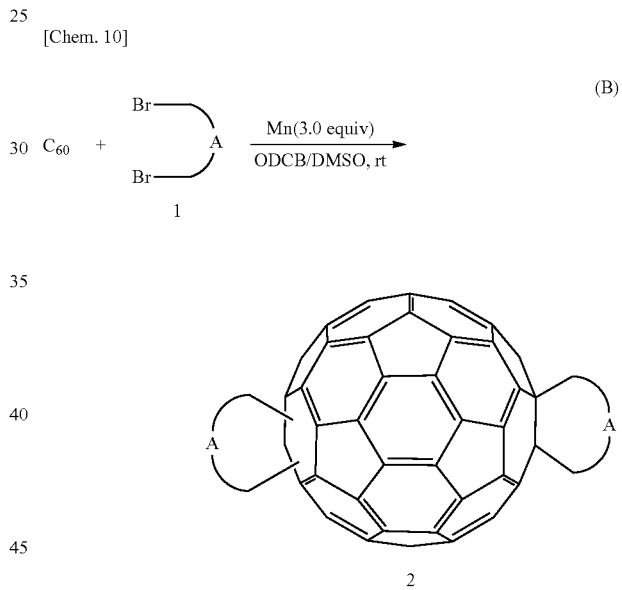

A reaction time, a used halogenated compound 1, an obtained fullerene derivative 2 and the yield thereof are shown in Table 2. The yield of the fullerene derivative was calculated by HPLC as in Example 1-1. Further, after an obtained fullerene derivative 2 was separated out, a $^1$H-NMR spectrum, a $^{13}$C-NMR spectrum and a HRMS spectrum were measured, and a compound was identified.

TABLE 2

| | HALOGENATED COMPOUND | | TIME (h) |
|---|---|---|---|
| EXAMPLE 2-1 | 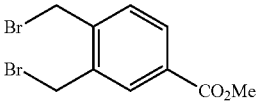 | (1b) | 47 |

TABLE 2-continued
| | | | |
|---|---|---|---|
| EXAMPLE 2-2 | 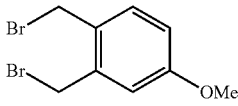 [SMILES: COc1ccc(CBr)c(CBr)c1] | (1c) | 38 |
| EXAMPLE 2-3 | 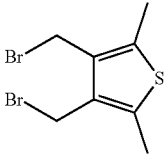 | (1d) | 15 |
| EXAMPLE 2-4 | 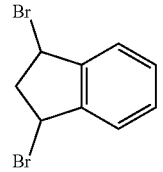 | (1e) | 23 |
| EXAMPLE 2-5 | 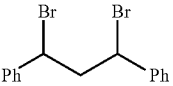 | (1f) | 12 |
| EXAMPLE 2-6 | 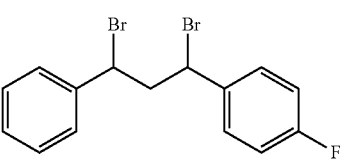 [SMILES: Fc1ccc(C(Br)CC(Br)c2ccccc2)cc1] | (1g) | 17 |
| EXAMPLE 2-7 | 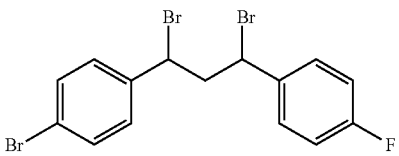 [SMILES: Fc1ccc(C(Br)CC(Br)c2ccc(Br)cc2)cc1] | (1h) | 12 |
| EXAMPLE 2-8 | 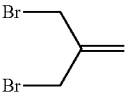 | (1i) | 47 |
| EXAMPLE 2-9 | 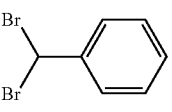 | (1j) | 18 |
| EXAMPLE 2-10 | 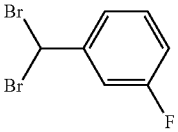 | (1k) | 24 |
| | FULLERENE DERIVATIVE (DICYCLIC ADDUCT) | | YIELD (%) |
|---|---|---|---|
| EXAMPLE 2-1 | 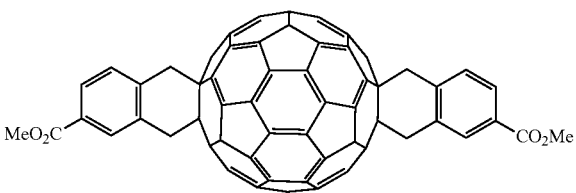 [SMILES: COC(=O)c1ccc2c(c1)CC1C3C=C4CC5=CC6C7c8c9c%10c%11c%12c%13c%14c%15c(c%16c%13c%13c(c4c5c7c%13c8%12)C%163)C1(CC%15=CC(C=C%10CC91Cc3ccc(C(=O)OC)cc3CC61)C%14%11)C2] | (2b) | 70 |

TABLE 2-continued
| EXAMPLE 2-2 | 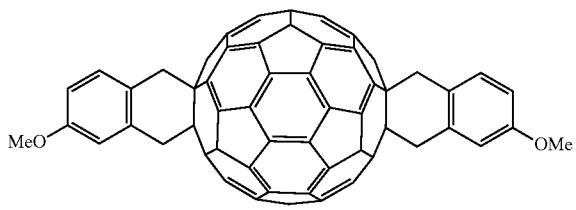 [SMILES: COc1ccc2c(c1)CC1C3C=C4CC5=CC6C7c8c9c%10c%11c%12c%13c%14c%15c(c%16c%13c%13c(c4c5c7c%13c8%12)C%163)C1(CC%15=CC(C=C%10CC91Cc3ccc(OC)cc3CC61)C%14%11)C2] | (2c) | 71 |
| EXAMPLE 2-3 | 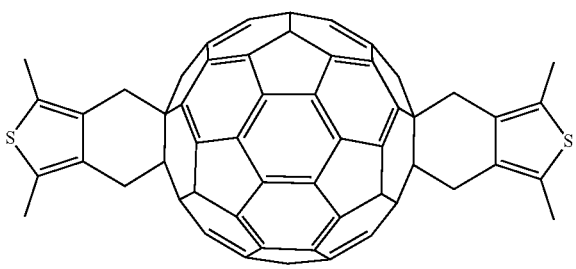 [SMILES: Cc1sc(C)c2c1CC1C3C=C4CC5=CC6C7c8c9c%10c%11c%12c%13c%14c%15c(c%16c%13c%13c(c4c5c7c%13c8%12)C%163)C1(CC%15=CC(C=C%10CC91Cc3c(C)sc(C)c3CC61)C%14%11)C2] | (2d) | 56 |
| EXAMPLE 2-4 | 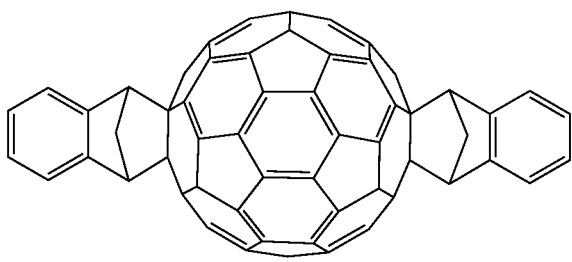 [SMILES: C1=C2CC34c5c2c2c6c7c8c9c%10c%11c7c7c%12c%13c%14c%15c7c6c5C%15C(C=C%14CC%13=CC(C%11%12)C5C6CC(c7ccccc76)C%105CC9=CC1C28)C3C1CC4c2ccccc21] | (2e) | 75 |
| EXAMPLE 2-5 | 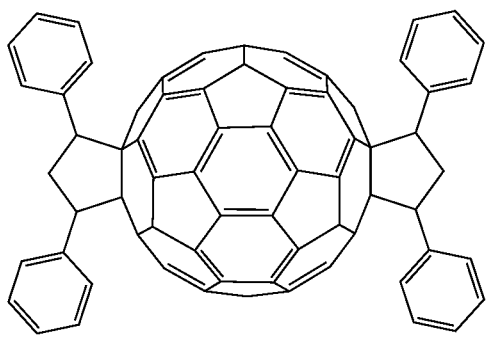 [SMILES: C1=C2CC34c5c2c2c6c7c8c9c%10c%11c7c7c%12c%13c%14c%15c7c6c5C%15C(C=C%14CC%13=CC(C%11%12)C5C(c6ccccc6)CC(c6ccccc6)C%105CC9=CC1C28)C3C(c1ccccc1)CC4c1ccccc1] | (2f) | 77 |
| EXAMPLE 2-6 | 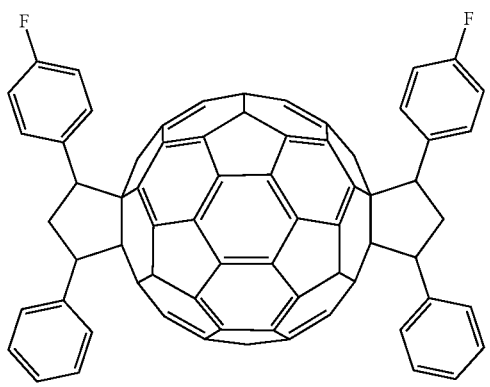 [SMILES: Fc1ccc(C2CC(c3ccccc3)C3C4C=C5CC6=CC7C8c9c%10c%11c%12c%13c%14c%15c%16c(c%17c%14c%14c(c5c6c8c%14c9%13)C%174)C23CC%16=CC(C=C%11CC%102C(c3ccc(F)cc3)CC(c3ccccc3)C72)C%15%12)cc1] | (2g) | 81 |

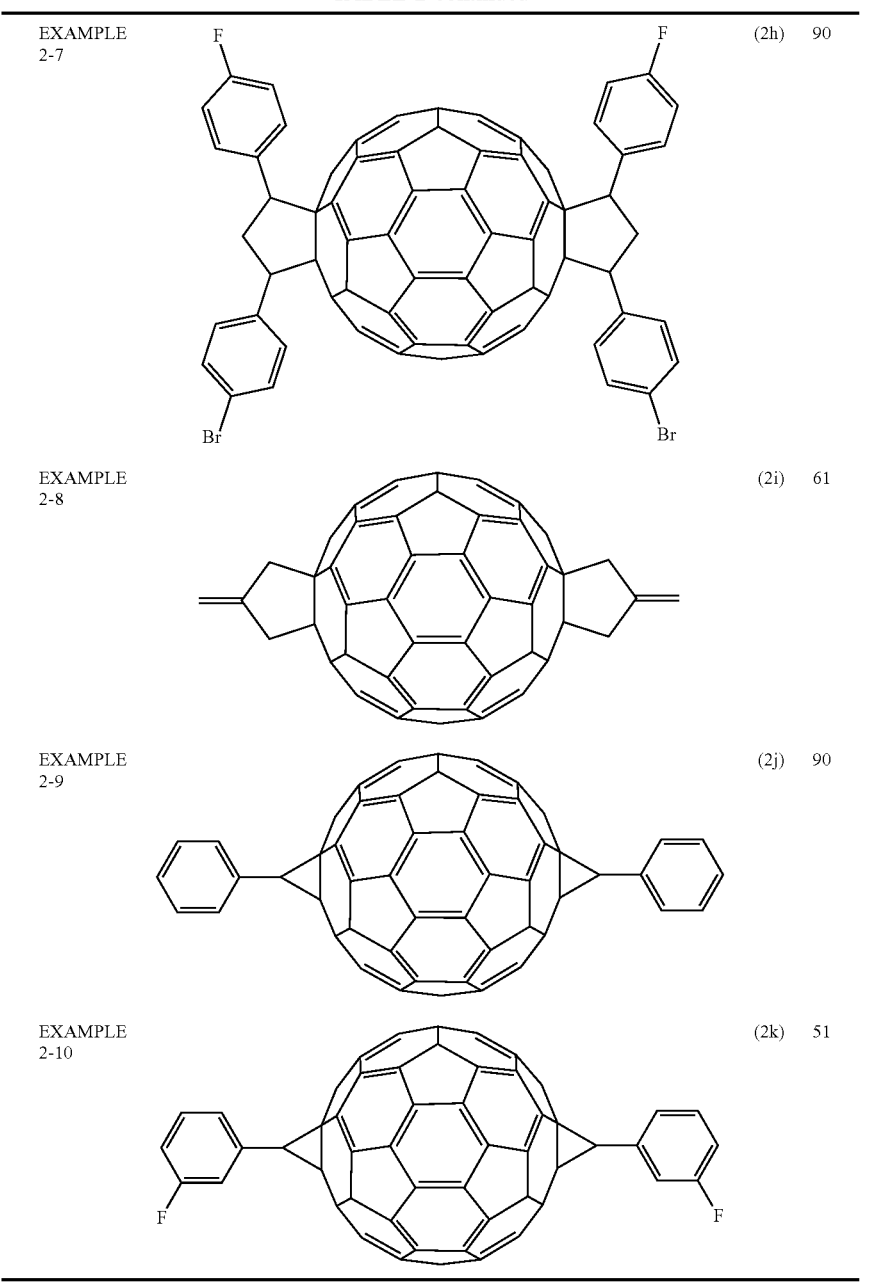

The data of each dicyclic adduct 2b to 2k is shown below.

2b: brown solid; $^1$H NMR (400 MHz, CDCl$_3$/CS$_2$=1/4) δ 3.94-4.13 (8H, m), 4.33-5.01 (6H, m), 7.27-8.51 (6H, m); $^{13}$C NM/R (100 MHz, CDCl$_3$/CS$_2$=1/4) δ 44.28, 44.65, 45.04, 51.76, 51.81, 63.73, 63.79, 63.86, 63.92, 64.10, 64.18, 64.43, 64.50, 127.46, 127.73, 128.77, 128.98, 129.57, 137.82, 139.40, 141.00, 141.11, 141.56, 142.38, 142.78, 143.42, 144.23, 144.43, 145.01, 145.60, 145.95, 146.33, 147.72, 148.23, 149.14, 154.01, 154.35, 156.74, 159.41, 160.24, 166.01; HRMS (MALDI) calcd for C$_{80}$H$_{20}$O$_4$[M]$^+$: 1044.1356, found 1044.1358.

2c: brown solid; $^1$H NMR (400 MHz, CDCl$_3$/CS$_2$=1/4) δ 3.72-4.91 (14H, m), 6.87-7.66 (6H, m); $^{13}$C NMR (100 MHz, CDCl$_3$/CS$_2$=1/4) δ 43.76, 44.09, 44.47, 44.79, 45.12, 45.50, 54.67, 54.70, 54.72, 63.84, 63.95, 63.97, 64.20, 64.23, 64.28, 64.34, 64.56, 64.61, 64.70, 64.92, 112.59, 113.29, 128.13, 128.40, 128.98, 129.40, 138.16, 138.55, 140.85, 141.05, 142.55, 143.29, 143.31, 144.10, 144.29, 144.45, 144.74, 144.98, 145.50, 145.83, 146.24, 146.25, 146.27, 146.35, 147.65, 148.16, 148.71, 149.04, 154.27, 154.29, 154.74, 158.82, 159.02, 159.82; HRMS (MALDI) calcd for C$_{88}$H$_{20}$O$_2$[M]$^+$: 1108.1458, found 1108.1463.

2d: brown solid; $^1$H NMR (400 MHz, CDCl$_3$/CS$_2$=1/4) δ 2.18-2.67 (12H, m), 3.85-4.51 (8H, m); $^{13}$C NMR (100 MHz, CDCl$_3$/CS$_2$=1/4) δ 12.32, 12.47, 12.53, 12.69, 38.94, 39.54, 39.85, 40.09, 40.27, 62.67, 63.87, 64.15, 64.31, 64.51, 129.10, 129.18, 129.47, 132.59, 132.71, 132.82, 132.98, 139.38, 140.90, 141.12, 141.34, 141.98, 142.57, 143.34, 144.02, 144.16, 144.28, 144.33, 144.52, 144.77, 145.01, 145.07, 145.36, 145.52, 145.94, 146.41, 146.75, 146.80, 147.31, 147.71, 148.19, 148.74, 148.84, 149.16, 149.98, 154.12, 155.04, 160.08, 161.17. HRMS (MALDI) $C_{76}H_{20}S_2[M]^+$: 996.1001, found: 996.1002.

2e: brown solid; $^1$H NMR (400 MHz, $CDCl_3/CS_2$=1/4) δ 2.45-4.05 (4H, m), 4.36-5.19 (4H, m), 7.09-7.82 (8H, m); $^{13}$C NMR (100 MHz, $CDCl_3/CS_2$=1/4) δ 45.18, 45.24, 45.80, 45.91, 5.99, 46.12, 46.31, 47.17, 56.99, 57.09, 57.13, 57.48, 57.51, 57.71, 57.74, 57.82, 57.90, 57.94, 58.06, 58.13, 58.15, 58.78, 73.32, 73.48, 73.54, 73.68, 73.77, 73.88, 74.10, 74.16, 74.25, 123.08, 123.10, 123.21, 123.26, 123.33, 123.43, 123.49, 123.62, 123.65, 123.69, 123.84, 123.96, 126.50, 126.64, 126.79, 126.87, 129.93, 127.02, 127.05, 127.09, 127.22, 127.25, 135.97, 136.12, 136.21, 136.28, 136.35, 136.40, 136.50, 136.54, 137.09, 137.12, 137.34, 140.63, 140.64, 140.70, 140.81, 140.84, 140.91, 141.50, 141.56, 141.71, 141.78, 141.86, 141.96, 142.01, 142.21, 143.21, 143.43, 143.57, 144.02, 144.10, 144.15, 144.17, 144.19, 144.31, 144.36, 144.41, 144.48, 144.51, 144.59, 144.64, 144.68, 144.72, 144.76, 144.84, 144.88, 145.15, 145.19, 145.27, 145.37, 145.39, 145.45, 145.49, 145.51, 145.66, 145.82, 146.14, 146.30, 146.56, 147.10, 147.12, 147.22, 147.26, 147.39, 147.54, 147.58, 147.76, 147.96, 148.04, 148.25, 148.33, 148.49, 154.21, 154.98, 155.56, 156.29, 156.47, 157.46, 158.77; HRMS (MALDI) $C_{78}H_{16}$ $[M]^+$: 952.1247, found: 952.1246.

2f: brown solid; $^1$H NMR (400 MHz, $CDCl_3/CS_2$=1/4) δ 2.62-5.69 (8H, m), 7.00-8.06 (20H, m); 13C NMR (100 MHz, $CDCl_3/CS_2$=1/4) δ 33.23, 34.13, 34.73, 34.89, 34.98, 35.20, 35.24, 35.28, 35.40, 36.71, 37.21, 37.34, 37.40, 57.00, 57.14, 57.29, 57.43, 57.58, 27.73, 57.99, 58.22, 58.31, 58.70, 58.82, 58.89, 58.95, 58.99, 59.07, 59.12, 59.18, 59.26, 59.43, 59.46, 59.54, 59.66, 59.69, 59.74, 59.80, 60.32, 74.01, 74.06, 74.15, 74.21, 74.27, 74.34, 74.40, 74.42, 74.44, 74.49, 74.53, 74.55, 74.59, 74.64, 74.77, 74.82, 74.86, 74.90, 75.11, 135.08, 137.33, 137.35, 137.47, 137.50, 137.65, 137.67, 137.73, 137.83, 137.89, 138.00, 138.22, 140.34, 140.45, 140.64, 140.87, 140.90, 140.97, 141.01, 141.07, 141.15, 142.13, 143.03, 143.71, 143.75, 144.05, 144.10, 144.12, 144.18, 144.25, 144.46, 144.56, 144.62, 144.73, 144.74, 144.82, 144.85, 145.31, 145.33, 145.48, 146.02, 146.48, 146.60, 147.19, 147.38, 147.47, 147.53, 147.62, 147.66, 147.76, 148.09, 148.21, 148.26, 148.33, 148.36, 148.43, 148.50, 148.54, 148.59, 148.61, 148.67, 152.17, 152.41, 153.99, 154.17, 154.28, 155.32, 155.42, 155.82, 155.96, 157.47. HRMS (MALDI) $C_{90}H_{28}$ $[M]^+$: 1108.2186, found: 1108.2187.

2g: brown solid; $^1$H NMR (400 MHz, $CDCl_3/CS_2$=1/4) δ 2.41-3.94 (4H, m), 4.19-5.72 (4H, m), 6.83-8.01 (18H, m); $^{13}$C NMR (100 MHz, $CDCl_3/CS_2$=1/4) δ 34.97, 5.13, 35.38, 35.46, 36.81, 37.35, 56.55, 56.62, 56.71, 57.19, 57.33, 57.45, 57.58, 57.62, 57.78, 58.10, 58.53, 58.82, 58.88, 59.08, 59.40, 59.59, 59.71, 73.82, 74.11, 74.14, 74.20, 74.29, 74.34, 74.43, 74.65, 74.86, 74.94, 114.47, 144.59, 114.68, 114.80, 114.87, 114.92, 115.02, 115.08, 115.15, 115.24, 115.30, 115.36, 115.43, 115.52, 127.00, 127.06, 127.09, 127.17, 127.25, 127.32, 127.41, 127.48, 127.58, 127.90, 127.94, 127.97, 128.04, 128.07, 128.13, 128.16, 128.20, 128.24, 128.26, 128.32, 128.37, 128.45, 128.53, 128.55, 128.58, 128.72, 128.76, 128.78, 128.81, 128.85, 128.86, 128.89, 128.93, 129.02, 129.05, 129.12, 129.24, 130.03, 130.11, 130.17, 130.23, 130.30, 130.34, 130.42, 130.52, 130.57, 130.60, 130.64, 130.71, 137.52, 140.89, 140.93, 143.84, 144.12, 144.53, 144.58, 144.66, 144.70, 145.28, 147.36, 147.57, 152.38, 153.58, 153.65, 154.17, 155.01, 155.11, 157.07, 157.26, 159.29, 160.33, 160.46, 160.53, 162.74, 162.99. HRMS (MALDI) $C_{90}H_{26}F_2[M]^+$: 1144.1997, found: 1144.1997.

2h: brown solid; $^1$H NMR (400 MHz, $CDCl_3/CS_2$=1/4) δ 2.38-3.91 (4H, m), 4.12-5.68 (4H, m), 6.90-7.88 (16H, m); 13C NMR (100 MHz, $CDCl_3/CS_2$=1/4) δ 33.34, 34.66, 34.86, 35.04, 35.41, 35.46, 36.43, 36.67, 56.43, 56.60, 56.70, 56.89, 56.98, 57.38, 57.46, 58.03, 58.07, 58.15, 58.21, 58.34, 58.41, 58.50, 58.78, 58.89, 59.04, 59.10, 73.61, 73.77, 73.82, 73.85, 74.00, 74.13, 74.28, 74.44, 74.59, 74.67, 114.29, 114.74, 114.92, 114.96, 115.16, 115.20, 115.30, 115.37, 115.51, 115.58, 121.53, 121.79, 121.84, 121.98, 122.01, 122.05, 122.13, 122.26, 129.87, 129.91, 129.95, 130.02, 130.04, 130.09, 130.22, 130.26, 130.29, 130.34, 130.39, 130.42, 130.51, 130.56, 130.61, 130.69, 130.74, 130.80, 131.04, 131.15, 131.28, 131.36, 131.46, 131.49, 131.56, 131.59, 131.69, 136.45, 136.78, 139.00, 140.60, 140.89, 141.02, 141.26, 141.70, 141.99, 143.11, 143.31, 143.66, 143.81, 143.85, 144.07, 144.19, 144.26, 144.51, 144.56, 144.58, 144.60, 144.69, 144.71, 144.74, 144.82, 145.29, 145.84, 146.38, 146.42, 146.49, 146.61, 147.11, 147.39, 147.66, 147.71, 147.83, 148.33, 148.41, 148.49, 148.70. HRMS (MALDI) $C_{90}H_{24}Br_2F_2$ $[M]^+$: 1300.0207, found 1300.0212.

2i: brown solid; $^1$H NMR (400 MHz, $CDCl_3/CS_2$=1/4) δ 3.32-4.57 (8H, m), 5.19-5.69 (4H, m); $^{13}$C NMR (100 MHz, $CDCl_3/CS_2$=1/4) δ 47.56, 47.64, 48.11, 48.37, 48.56, 67.83, 67.88, 68.07, 68.24, 68.29, 109.55, 110.06, 134.47, 134.52, 135.45, 136.32, 137.59, 139.46, 139.80, 140.18, 140.74, 140.79, 140.85, 141.06, 141.16, 141.18, 142.20, 142.82, 143.19, 143.25, 143.37, 143.55, 143.70, 144.04, 144.06, 144.22, 144.35, 144.37, 144.42, 144.65, 144.72, 144.87, 144.95, 144.97, 145.05, 145.35, 145.69, 145.75, 146.36, 146.87, 147.43, 147.67, 147.82, 147.91, 148.04, 148.26, 148.53, 148.56, 148.74, 153.87, 154.37, 154.81, 156.18, 156.94, 156.95, 159.78, 160.36. HRMS (MALDI) $C_{68}H_{12}$ $[M]^+$: 828.0934, found: 828.0934.

2j: brown solid; $^1$H NMR (400 MHz, $CDCl_3/CS_2$=1/4) δ 4.54-5.50 (2H, m), 7.26-8.19 (10H, m); 13C NMR (100 MHz, $CDCl_3/CS_2$=1/4) δ 40.88, 40.94, 41.03, 41.07, 41.23, 41.90, 42.35, 42.42, 42.55, 44.56, 45.12, 70.57, 73.02, 74.29, 74.38, 74.43, 74.59, 74.62, 74.67, 75.01, 75.12, 75.14, 75.25, 75.74, 75.78, 75.86, 75.90, 127.83, 127.87, 127.90, 127.92, 127.97, 128.02, 128.04, 128.14, 128.24, 128.33, 128.38, 128.41, 128.44, 128.60, 130.27, 130.50, 130.60, 130.63, 130.73, 130.75, 130.77, 130.84, 130.87, 130.92, 131.03, 132.05, 132.43, 132.56, 132.61, 132.63, 132.67, 132.80, 132.94, 132.97, 133.07, 133.10, 137.52, 137.59, 137.87, 137.95, 138.00, 138.05, 138.20, 138.32, 138.64, 138.71, 138.76, 138.82, 139.04, 139.16, 139.27, 139.35, 139.48, 139.51, 139.76, 140.96, 141.12, 141.21, 141.28, 141.31, 141.36, 141.51, 141.90, 141.92, 142.20, 142.55, 142.64, 142.91, 142.93, 142.95, 142.96, 143.40, 143.43, 143.52, 143.53, 143.56, 143.65, 143.74, 143.76, 143.78, 143.80, 143.83, 143.90, 143.94, 144.00, 144.02, 144.09, 144.14, 144.16, 144.25, 144.32, 144.35, 144.51, 144.68, 144.72, 144.76, 144.87, 144.98, 145.12, 145.37, 145.47, 145.64, 145.76, 145.78, 145.85, 145.88, 145.90, 145.92, 145.94, 146.02, 146.04, 146.06, 146.11, 146.19, 146.21, 147.21, 147.39, 147.93, 150.40, 151.13. HRMS (MALDI) $C_{74}H_{12}$ $[M]^+$: 900.0934, found: 900.0934.

2k: brown solid; $^1$H NMR (400 MHz, $CDCl_3/CS_2$=1/4) δ 4.47-5.47 (2H, m), 7.05-7.24 (2H, m), 7.39-7.99 (6H, m); $^{13}$C NMR (100 MHz, $CDCl_3/CS_2$=1/4) δ 40.00, 40.03, 40.15, 40.27, 40.28, 40.44, 40.50, 41.02, 41.50, 41.53, 41.56, 41.58, 41.73, 41.75, 43.66, 43.69, 44.24, 44.27, 69.96, 72.54, 73.07, 73.40, 73.67, 73.74, 73.97, 74.01, 74.09, 74.21, 74.25, 74.30, 74.67, 74.77, 74.88, 75.28, 75.30, 75.33, 75.41, 75.49, 114.89, 114.92, 114.96, 114.01, 114.07, 115.10, 115.13, 115.17, 115.21, 115.28, 115.39, 117.43, 117.45, 117.56, 117.66, 117.71, 117.78, 117.82, 117.87, 117.89, 117.93, 117.98, 118.01, 118.03, 118.19, 125.92, 125.94, 126.17, 126.20, 126.27, 126.30, 126.40, 126.43, 126.46, 126.51, 126.54, 126.56, 126.70, 126.73, 129.77, 129.85, 129.89, 129.94, 129.97, 130.05, 130.13, 130.21, 131.75, 133.29, 133.58, 133.68, 133.87, 134.38, 134.45, 134.69, 134.76, 134.79, 134.84, 134.90, 134.98, 135.01, 135.05, 135.09, 135.13, 135.20, 135.31, 135.36, 135.43, 135.62, 135.71, 135.86, 136.00, 136.06, 136.16, 136.28, 136.39, 136.61, 136.78, 137.54, 137.63, 138.04, 138.29, 138.39, 138.73, 138.80, 139.22, 139.30, 139.38, 139.40, 139.54, 139.77, 140.02, 140.31, 140.65, 140.69, 140.72, 140.95, 141.14, 141.29, 141.31, 141.37, 141.39, 141.41, 141.44, 141.49, 141.51, 141.54, 141.59, 141.64, 141.89, 141.91, 141.93, 142.30, 142.48, 142.50, 142.52, 142.62, 142.70, 142.81, 142.82, 142.94, 142.96, 142.98, 143.00, 143.02, 143.04, 143.15, 143.22, 143.28, 143.32, 143.34, 143.38, 143.42, 143.46, 143.49, 143.52, 143.54, 143.60, 143.75, 143.80, 143.83, 143.85, 143.87, 143.91, 143.97, 144.07, 144.09, 144.11, 144.15, 144.22, 144.23, 144.28, 144.31, 144.33, 144.39, 144.42, 144.52, 144.61, 144.63, 144.67, 144.72, 144.76, 144.80, 144.84, 144.86, 144.88, 144.95, 144.98, 145.00, 145.06, 145.09, 145.11, 145.12, 145.15, 145.28, 145.31, 145.33, 145.35, 145.50, 145.51, 145.55, 145.60, 145.68, 145.73, 145.76, 145.78, 145.81, 145.83, 145.88, 145.90, 145.99, 146.01, 146.02, 146.13, 146.42, 146.48, 146.69, 146.78, 146.83, 146.87, 146.94, 146.96, 147.04, 147.06, 147.21, 147.29, 147.43, 147.48, 147.57, 147.61, 147.75, 147.80, 148.16, 148.31, 148.70, 149.07, 149.13, 149.42, 149.52, 149.55, 149.71, 149.76, 149.82, 150.03, 150.13, 150.80, 151.50, 160.92, 60.97, 161.02, 161.18, 163.32, 163.40, 163.44, 163.50, 163.64. HRMS (MALDI) $C_{74}H_{10}F_2[M^+Na]^+$: 936.0745, found 976.0743.

When Example 2-1 is compared with Example 2-2, there is a difference in that methyl added to a cyclic adduct is bound by an ester bond or an ether bond. However, it was found that each yield was almost the same, and an electron withdrawing property and an electron donating property do not greatly affect the selectivity for a fullerene derivative. Further, even a compound having a heteroaromatic ring or a plurality of aromatic rings such as fullerene derivatives 2d, 2f, 2g and 2h obtained in Examples 2-3, 2-5, 2-6 and 2-7 can be obtained.

Examples 3-1 to 3-8

In Examples 3-1 to 3-8, a monocyclic adduct in which one cyclic substance is added to a fullerene skeleton was selectively prepared as a fullerene derivative.

$C_{60}$ (21.6 mg, 0.03 mmol) was used as a compound having a fullerene skeleton and reacted with a halogenated compound (1.0 mol equivalent). At this time, ODCB (4 mL) as an aromatic solvent and DMSO (0.4 mL) as an aprotic polar solvent were used for the mixed solution. Moreover, Mn powder (1.0 mol equivalent) was used as a metal used in the reaction, and the reaction of Reaction Formula (C) was performed at room temperature under an Ar atmosphere.

[Chem. 11]

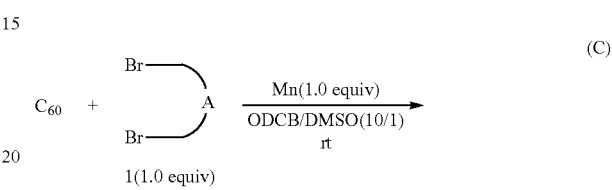

(C)

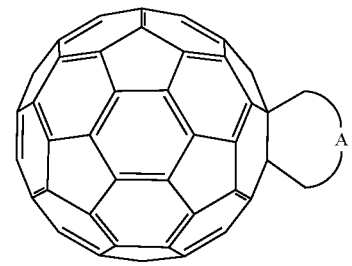

3,monocycloadducts

A reaction time, a used halogenated compound 1, an obtained fullerene derivative 3 and the yield thereof are shown in Table 3. The yield of the fullerene derivative was calculated by HPLC as in Example 1-1. Further, after an obtained fullerene derivative 3 was separated out, a $^1$H-NMR spectrum, a $^{13}$C-NMR spectrum and a HRMS spectrum were measured, and a compound was identified.

TABLE 3

| | HALOGENATED COMPOUND | TIME (h) | FULLERENE DERIVATIVE (MONOCYCLIC ADDUCT) | YIELD (%) |
|---|---|---|---|---|
| EXAMPLE 3-1 | ![Br-CH2-C6H4-CH2-Br] (1a) | 12 | ![fullerene indane adduct] (3a) | 72 |

TABLE 3-continued
| | HALOGENATED COMPOUND | | TIME (h) | FULLERENE DERIVATIVE (MONOCYCLIC ADDUCT) | | YIELD (%) |
|---|---|---|---|---|---|---|
| EXAMPLE 3-2 | 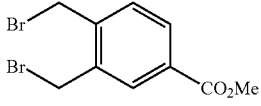 [SMILES: COC(=O)c1ccc(CBr)c(CBr)c1] | (1b) | 12 | 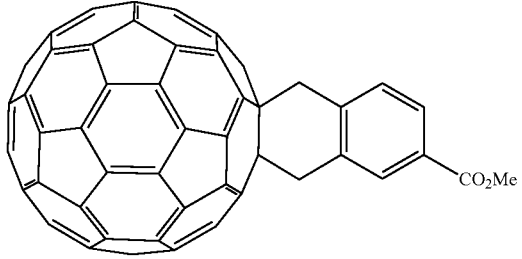 [SMILES: COC(=O)c1ccc2c(c1)CC1c3cc4c5c6c(cc7cc8c9c%10c(cc%11cc%12c%13c(c%14c3c5c3c%14c5c%13c%11c%10c5c5c9c7c6c35)C1(C2)C%12)C8)C4] | (3b) | 82 |
| EXAMPLE 3-3 | 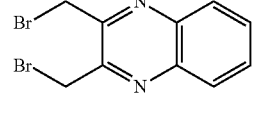 | (1m) | 21 | 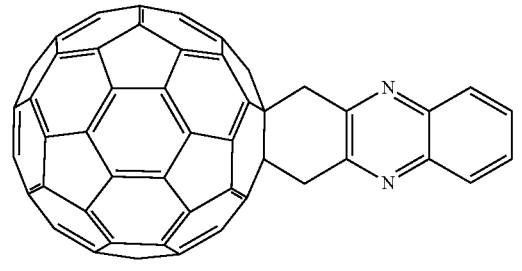 [SMILES: c1ccc2nc3c(nc2c1)CC1c2cc4c5c6c(cc7cc8c9c%10c(cc%11cc%12c%13c(c%14c2c5c2c%14c5c%13c%11c%10c5c5c9c7c6c25)C1(C3)C%12)C8)C4] | (3m) | 50 |
| EXAMPLE 3-4 | 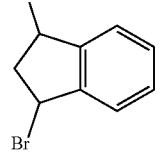 | (1e) | 24 | 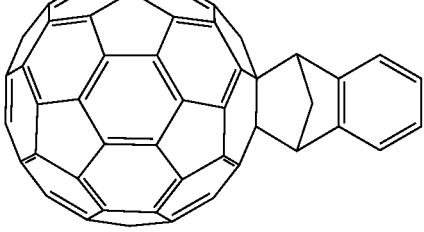 | (3e) | 74 |
| EXAMPLE 3-5 | 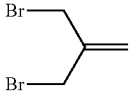 | (1i) | 48 | 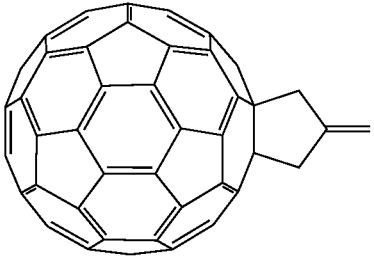 [SMILES: C=C1CC2c3cc4c5c6c(cc7cc8c9c%10c(cc%11cc%12c%13c(c%14c3c5c3c%14c5c%13c%11c%10c5c5c9c7c6c35)C2(C1)C%12)C8)C4] | (3i) | 60 |
| EXAMPLE 3-6 | 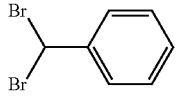 | (1j) | 24 | 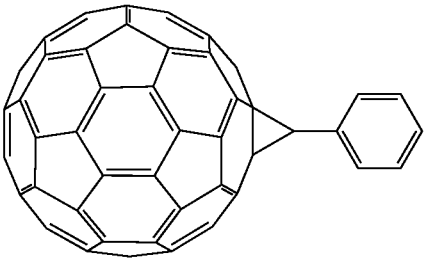 [SMILES: c1ccc(C2C3c4cc5c6c7c(cc8cc9c%10c%11c(cc%12cc%13c%14c(c%15c4c6c4c%15c6c%14c%12c%11c6c6c%10c8c7c46)C23C%13)C9)C5)cc1] | (3j) | 81 |

TABLE 3-continued

| | HALOGENATED COMPOUND | TIME (h) | | FULLERENE DERIVATIVE (MONOCYCLIC ADDUCT) | | YIELD (%) |
|---|---|---|---|---|---|---|
| EXAMPLE 3-7 | [Br-CH(Br)-C6H4-F structure] | (1k) | 12 | [fullerene with cyclopropane-phenyl-F] | (3k) | 75 |
| EXAMPLE 3-8 | [Br-CH(Br)-CO2Et structure] | (1l) | 21 | [fullerene with cyclopropane-CO2Et] | (3l) | 40 |

It can be seen from Examples 3-1 to 3-8 that a monocyclic adduct was obtained selectively. This is considered to be because the amount of a metal content used in the reaction and/or a halogenated compound was reduced.

A fullerene derivative 3b prepared using 3,4-bis(bromomethyl)benzoic acid methylbenzene 1b in Example 3-2 showed a yield of 82%, which is much higher than that of 64% of a conventional method using a Co complex. While it was impossible to obtain a fullerene derivative 3c of Example 3-3 using the conventional method using a Co complex because the reaction does not proceed, the fullerene derivative 3c of Example 3-3 showed a high yield of 50% using the method of the present invention. It was also possible to obtain other fullerene derivatives in a relatively higher yield than in the conventional method using a Co complex. It was impossible to obtain a fullerene derivative 3l of Example 3-8 using the conventional method using a Co complex. That is, the reaction can proceed without using an expensive Co complex, selectivity is increased, and a compound which could not be obtained conventionally can also be obtained by using the method of the present invention.

Example 4-1

In Example 4-1, phenyl-C61-butyric acid methyl ester (hereinafter, referred to as "[60] PCBM") was synthesized as a fullerene derivative. Furthermore, [60] PCBM is a monocyclic adduct in which one cyclic substance is added to a fullerene skeleton.

Synthesis of 5,5-dibromo-5-phenylvaleric acid methyl ester: After n-bromosuccinimide (1.95 g, 11 mmol) and a small amount of azobisisobutyronitrile were added to a solution of methyl 5-phenylvalerate (manufactured by Tokyo Chemical Industry Co., Ltd., 0.95 mL, 5 mmol) in carbon tetrachloride (50 mL) under an argon atmosphere, heating under reflux was conducted with stirring for 2 hours to perform a reaction. After the reaction, a product was cooled to room temperature, insolubles were removed by filtration, and cleaning was performed using carbon tetrachloride. After a solvent was distilled off, a concentrate was recrystallized from a mixed solvent of ethyl acetate and hexane, and 5,5-dibromo-5-phenylvaleric acid methyl ester was obtained as white crystals in a yield of 90%.

Synthesis of [60] PCBM: $C_{60}$ (21.6 mg, 0.03 mmol) was used as a compound having a fullerene skeleton and reacted with 5,5-dibromo-5-phenylvaleric acid methyl ester (1.2 mol equivalents) as a halogenated compound. At this time, ODCB (6 mL) as an aromatic solvent and DMSO (0.4 mL) as an aprotic polar solvent were used for the mixed solution. Moreover, Mn powder (1.5 mol equivalents) was used as a metal used in the reaction, and the reaction of Reaction Formula (D) was performed under an Ar atmosphere for 7 hours.

[Chem. 12]

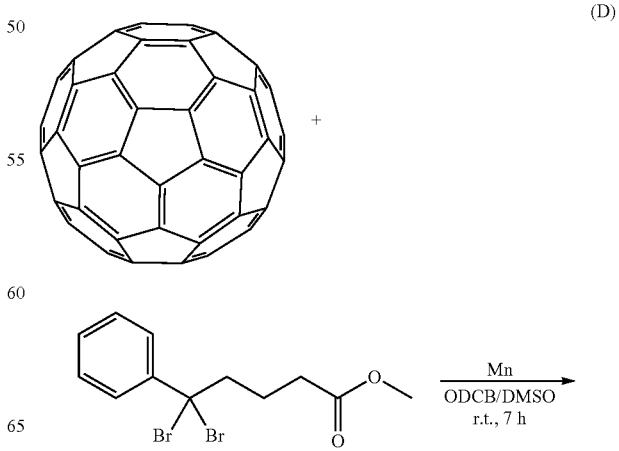

(D)

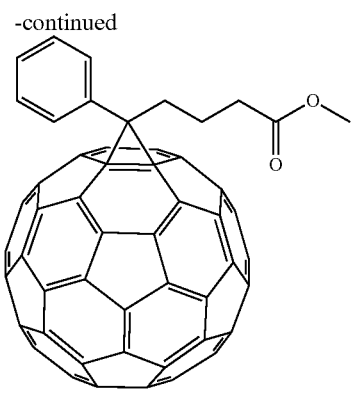

A yield of [60] PCBM, as a result of calculation by HPLC as in Example 1-1, was 98%. Further, after the obtained [60] PCBM was separated out, a $^1$H-NMR spectrum and a $^{13}$C-NMR spectrum were measured and a compound was identified.

The data thus obtained is shown below.

[60] PCBM: brown solid; $^1$H NMR (400 MHz, CDCl$_3$/CS$_2$=1/4) δ 2.15-2.23 (2H, m), 2.52 (2H, t, J=7.2 Hz), 2.90-2.93 (2H, m), 3.67 (3H, s), 7.47 ($^1$H, dd, J=7.2, 7.6 Hz), 7.54 (2H, dd, J=7.2, 7.6 Hz) 7.91 (2H, d, J=7.2 Hz); $^{13}$C NMR (100 MHz, CDCl$_3$/CS$_2$=1/4) δ 22.39, 33.58, 33.71, 52.27, 51.62, 128.01, 128.22, 131.75, 136.33, 137.35, 137.75, 140.48, 140.72, 141.78, 141.81, 141.88, 142.63, 142.69, 142.74, 142.81, 143.44, 143.76, 144.14, 144.18, 144.34, 144.37, 144.45, 144.46, 144.71, 144.74, 144.84, 144.87, 145.48, 147.35, 148.28.

In this manner, it is possible to prepare [60] PCBM from a fullerene which is a raw material in one process when the method of the present invention is used. Further, it was prepared in a yield of 57% from C$_{60}$ as a raw material through a reaction of two steps with the conventional synthesis method of [60] PCBM (e.g., a method described in Non patent literature 1). [60] PCBM is suitably used as an organic thin film solar cell material, and thus the method of the present invention by which [60] PCBM can be prepared in a high yield without wasting an expensive raw material is of extremely great industrial value.

INDUSTRIAL APPLICABILITY

The fullerene derivative of the present invention is applicable to various usages such as electronic materials such as organic solar cells, resin additives, and so on.

What is claimed is:
1. A halogenated compound being a 5,5-dibromo-5-phenylvaleric acid methyl ester.

* * * * *

UNITED STATES PATENT AND TRADEMARK OFFICE
CERTIFICATE OF CORRECTION

PATENT NO. : 11,136,298 B2
APPLICATION NO. : 16/680570
DATED : October 5, 2021
INVENTOR(S) : Tienan Jin et al.

It is certified that error appears in the above-identified patent and that said Letters Patent is hereby corrected as shown below:

On the Title Page

Delete the title page and replace with the attached title page showing the corrected number of claims In the Claims Insert the following Claims 2-8 after Column 28, Line 26 (i.e., after Claim 1):

--2. A method for producing a fullerene derivative having a partial structure represented by Formula (1), by reacting two carbon atoms adjacent to each other for forming a fullerene skeleton with a halogenated compound according to Claim 1 in a mixed solvent of an aromatic solvent and an aprotic polar solvent having a C=O or S=O bond in the presence of at least one metal selected from the group consisting of manganese, iron and zinc:

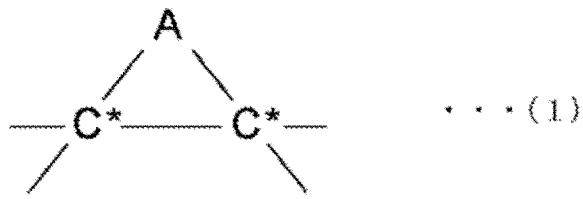

(in Formula (1), C* each represent carbon atoms adjacent to each other for forming a fullerene skeleton, and A represents a linking group with 1 carbon atom for forming a ring structure in which the linking group is substituted by a phenyl group and -$(CH_2)_3$-CO-O-$CH_3$.

3. The method for producing a fullerene derivative according to Claim 2, wherein
  a compound having the fullerene skeleton is reacted with the halogenated compound, and
  $C_{60}$ is used as the compound having the fullerene skeleton.

4. The method for producing a fullerene derivative according to Claim 2, wherein the aprotic polar solvent consists of dimethyl sulfoxide (DMSO) and/or dimethylformamide (DMF).

Signed and Sealed this
Thirty-first Day of May, 2022

Katherine Kelly Vidal
*Director of the United States Patent and Trademark Office*

5. The method for producing a fullerene derivative according to Claim 2, wherein the aromatic solvent is o-dichlorobenzene.

6. The method for producing a fullerene derivative according to Claim 2, wherein the metal is Mn, and the aprotic polar solvent is DMF.

7. The method for producing a fullerene derivative according to Claim 2, wherein the metal is Fe, and the aprotic polar solvent is DMSO.

8. The method for producing a fullerene derivative according to Claim 2, wherein the metal is Mn or Zn, and the aprotic polar solvent is DMSO.--

(12) United States Patent
Jin et al.

(10) Patent No.: US 11,136,298 B2
(45) Date of Patent: *Oct. 5, 2021

(54) METHOD FOR PRODUCING FULLERENE DERIVATIVE

(71) Applicants: SHOWA DENKO K.K., Tokyo (JP); MITSUBISHI CORPORATION, Tokyo (JP)

(72) Inventors: Tienan Jin, Sendai (JP); Weili Si, Boulder, CO (US); Yoshinori Yamamoto, Sendai (JP); Takeshi Igarashi, Chiba (JP)

(73) Assignees: SHOWA DENKO K.K., Tokyo (JP); MITSUBISHI CORPORATION, Tokyo (JP)

(*) Notice: Subject to any disclaimer, the term of this patent is extended or adjusted under 35 U.S.C. 154(b) by 0 days.

This patent is subject to a terminal disclaimer.

(21) Appl. No.: 16/680,570

(22) Filed: Nov. 12, 2019

(65) Prior Publication Data
US 2020/0095209 A1  Mar. 26, 2020

Related U.S. Application Data

(62) Division of application No. 15/509,080, filed as application No. PCT/JP2015/075186 on Sep. 4, 2015, now Pat. No. 10,526,293.

(30) Foreign Application Priority Data

Sep. 8, 2014 (JP) ................... 2014-182133
Oct. 22, 2014 (JP) ................... 2014-215192

(51) Int. Cl.
| | | |
|---|---|---|
| C07C 22/04 | (2006.01) | |
| C07D 241/38 | (2006.01) | |
| C01B 32/154 | (2017.01) | |
| C07C 67/343 | (2006.01) | |
| C07C 69/76 | (2006.01) | |
| C07C 41/30 | (2006.01) | |
| C07C 43/21 | (2006.01) | |
| C07D 333/78 | (2006.01) | |
| C07C 1/26 | (2006.01) | |
| C07C 2/86 | (2006.01) | |
| C07D 241/36 | (2006.01) | |
| C07C 13/64 | (2006.01) | |
| C07C 17/266 | (2006.01) | |
| C07C 17/32 | (2006.01) | |
| C07C 25/22 | (2006.01) | |
| C07D 241/42 | (2006.01) | |
| A61K 31/5377 | (2006.01) | |

(Continued)

(52) U.S. Cl.
CPC ........ *C07D 241/38* (2013.01); *A61K 31/5377* (2013.01); *A61K 31/55* (2013.01); *C01B 32/154* (2017.08); *C07C 1/26* (2013.01); *C07C 2/86* (2013.01); *C07C 13/64* (2013.01); *C07C 17/266* (2013.01); *C07C 17/32* (2013.01); *C07C 25/22* (2013.01); *C07C 41/30* (2013.01); *C07C 43/21* (2013.01); *C07C 67/343* (2013.01); *C07C 69/76* (2013.01); *C07D 241/36* (2013.01); *C07D 241/42* (2013.01); *C07D 333/78* (2013.01); *C07B 61/00* (2013.01); *C07C 2523/06* (2013.01); *C07C 2523/34* (2013.01); *C07C 2523/745* (2013.01); *C07C 2604/00* (2017.05)

(58) Field of Classification Search
None
See application file for complete search history.

(56) References Cited

U.S. PATENT DOCUMENTS 4,265,891 A  5/1981  Collington et al.
4,649,212 A  3/1987  Durr
(Continued)

FOREIGN PATENT DOCUMENTS

EP  2457898 A1  5/2012
JP  55-36475 A  3/1980
(Continued)

OTHER PUBLICATIONS

Database Registry Chemical Abstracts Service, Columbus, Ohio, Accession No. RN 135100-98-0, Entered STN: Jul. 26, 1991.*
(Continued)

*Primary Examiner* — Samantha L Shterengarts
(74) *Attorney, Agent, or Firm* — Sughrue Mion, PLLC

(57) ABSTRACT

This method for producing a fullerene derivative is a method for producing a fullerene derivative having a partial structure shown by formula (1) by reacting a predetermined halogenated compound and two carbon atoms adjacent to each other for forming a fullerene skeleton in a mixed solvent of an aromatic solvent and an aprotic polar solvent having a C=O or S=O bond in the presence of at least one metal selected from the group comprising manganese, iron, and zinc;

[Chem. 1]

(1)

(in formula (1), C* are each carbon atoms adjacent to each other for forming a fullerene skeleton, A is a linking group having 1-4 carbon atoms for forming a ring structure with two C*, in which a portion thereof may be a substituted or condensed group).

8 Claim, No Drawings